United States Patent
Du Toit et al.

(10) Patent No.: US 10,233,414 B2
(45) Date of Patent: Mar. 19, 2019

(54) METHOD OF PRODUCING A FERMENTED BEVERAGE

(71) Applicant: Stellenbosch University, Stellenbosch (ZA)

(72) Inventors: Wessel Johannes Du Toit, Somerset West (ZA); Sebastian Vannevel, Passendale (BE)

(73) Assignee: Stellenbosch University, Stellenbosch (ZA)

( * ) Notice: Subject to any disclaimer, the term of this patent is extended or adjusted under 35 U.S.C. 154(b) by 22 days.

(21) Appl. No.: 15/649,075

(22) Filed: Jul. 13, 2017

(65) Prior Publication Data

US 2018/0016532 A1    Jan. 18, 2018

(30) Foreign Application Priority Data

Jul. 13, 2016  (ZA) .................................. 201604801

(51) Int. Cl.
| | | |
|---|---|---|
| *C12G 1/02* | (2006.01) | |
| *C12G 1/04* | (2006.01) | |
| *C12G 3/02* | (2019.01) | |
| *C12G 3/08* | (2006.01) | |
| *C12P 11/00* | (2006.01) | |
| *C12C 5/00* | (2006.01) | |
| *C12C 5/02* | (2006.01) | |

(52) U.S. Cl.
CPC .................. *C12G 1/02* (2013.01); *C12C 5/00* (2013.01); *C12C 5/026* (2013.01); *C12G 1/0203* (2013.01); *C12G 1/04* (2013.01); *C12G 3/02* (2013.01); *C12G 3/08* (2013.01); *C12P 11/00* (2013.01); *C12G 2200/21* (2013.01)

(58) Field of Classification Search
CPC ........ C12G 1/02; C12G 1/04; C12G 2200/21; C12C 5/026; C12P 11/00
USPC .............. 426/15, 11, 16, 615, 592, 600, 493
See application file for complete search history.

(56) References Cited

FOREIGN PATENT DOCUMENTS

EP            2554650 A1    2/2013

*Primary Examiner* — Helen F Heggestad
(74) *Attorney, Agent, or Firm* — Workman Nydegger (57) ABSTRACT

A method for preparing a fermented beverage having a modulated aromatic profile is provided as well as a fermented beverage produced thereby. The method includes preparing a fermentable mixture, such as juice, must, or wort and introducing ammonium sulphide into the fermentable mixture at a predetermined concentration. The fermentable mixture is then subjected to fermentation. A C6 aldehyde, C6 alcohol or a combination thereof may be added to the fermentable mixture in combination with ammonium sulphide to enhance its effect on the aromatic profile of the fermented beverage.

20 Claims, 10 Drawing Sheets

METHOD OF PRODUCING A FERMENTED BEVERAGE

CROSS-REFERENCE TO RELATED APPLICATIONS

The present invention claims the benefit of priority to the South African Patent Application No. 2016/04801 filed Jul. 13, 2016 entitled "METHOD OF PRODUCING A FERMENTED BEVERAGE;" the entire content of which is incorporated herein by reference.

BACKGROUND OF THE INVENTION

1. The Field of the Invention

This invention relates to a method of producing fermented beverages. More specifically, it relates to a method for producing fermented beverages such as wine, beer and cider.

2. Background and Relevant Art

The aromatic profile of a fermented beverage is considered a major factor in determining its perception by the consumer thereof. This is particularly relevant in the case of grape derived wines.

The aromatic profile of wine is the result of a complex process of aroma development having numerous variables and inputs from the vineyard as well as the cellar. These variables include the particular grape cultivar, terroir, the particular strain of yeast responsible for the fermentation and various methods employed by the winemaker, to name but a few.

Sauvignon Blanc is a grape cultivar that has been, and remains, the subject of considerable research. Two classes of compounds that are considered key in determining the aroma of Sauvignon Blanc are methoxypyrazines and varietal thiols. The green or capsicum aromas of Sauvignon Blanc can be attributed to methoxypyrazines which are stable compounds. Varietal thiols are present in grapes as odourless precursors and are either released by enzymes in the mouth or by yeasts during fermentation. These volatile compounds are believed to be responsible for the fruity, stalk, sweat and cat urine aromas associated with Sauvignon Blanc, the fruity aroma being the desirable aromatic element. In this regard, the 3-mercaptohexanol (3MH) and 3-mercaptohexylacetate (3MHA) varietal thiols are notable compounds.

The 3MH volatile thiol is believed to be responsible for passion fruit, grapefruit and general citrus aromas, whereas 3MHA is believed to be responsible for passion fruit, gooseberry, guava and other tropical fruit aromas at lower levels.

While these compounds contribute significantly to the aromatic profile of Sauvignon Blanc, they also contribute to that of other wine cultivars, including Chenin Blanc, Riesling, Pinot Gris, Gewürztraminer, Cabernet Sauvignon, Merlot, Shiraz and Grenache.

To date, the complex processes involved in the development of the aromatic profiles of wines are not fully understood. Methods to produce a desired aromatic profile in the end product are limited and remain a significant topic of research.

EP2554650A1 discloses a method of producing an alcoholic beverage having a fruity flavour. The method includes the bubbling of a gas stream containing hydrogen sulphide (H2S) into grape juice prior to inoculation by yeast, and/or during fermentation. This method is disadvantageous in so far as H2S is a highly toxic, broad-spectrum poison. The danger is aggravated by the fact that inhalation of H2S at concentrations of 100-150 parts per million (ppm) incapacitates the sense of smell and therefore also the indication of danger. This method therefore may require additional safety equipment. Furthermore, it may be problematic to accurately control the concentration of H2S taken up by the fermentable mixture.

The invention disclosed herein aims to address some of the abovementioned drawbacks, at least to some extent.

The preceding discussion of the background to the invention is intended only to facilitate an understanding of the present invention. It should be appreciated that the discussion is not an acknowledgment or admission that any of the material referred to was part of the common general knowledge in the art as at the priority date of the application

BRIEF SUMMARY OF THE INVENTION

In accordance with the invention there is provided a method for preparing a fermented beverage having a modulated aromatic profile, the method including: preparing a fermentable mixture; introducing ammonium sulphide into the fermentable mixture to obtain a predetermined concentration of ammonium sulphide in the fermentable mixture; and subjecting the fermentable mixture to fermentation.

Further features of the invention provide for an aqueous solution of ammonium sulphide to be introduced into the fermentable mixture; for the predetermined concentration to be between about 1.5 and 50 milligrams per litre (mg/L), preferably between about 1.5 and 6.5 mg/L; and for the method to further include the additional step of allowing between about 1 and 24 hours, preferably about 24 hours, of contact time between the fermentable mixture and the ammonium sulphide prior to subjecting the fermentable mixture to fermentation.

Yet further features of the invention provide for a C6 aldehyde, a C6 alcohol or a combination thereof to be introduced into the fermentable mixture before subjecting the fermentable mixture to fermentation; for the C6 aldehyde to be (E)-2-hexenal; for the (E)-2-hexenal to be introduced into the fermentable mixture in an amount to obtain a concentration of between about 0.5 and 3 mg/L thereof in the fermentable mixture; for the C6 alcohol to be (E)-2-hexenol; and for the (E)-2-hexenol to be introduced into the fermentable mixture in an amount to obtain a concentration of between about 7 and 15 mg/L thereof in the fermentable mixture.

Still further features of the invention provide for the fermentable mixture to be fruit juice, must, or wort; for the fruit juice to be white grape juice or red grape juice; for the fruit juice to be the juice of white or red grapes of the *Vitis vinifera* species; for the fruit juice to be juice from Sauvignon Blanc grapes; and for the fruit juice to be turbid.

In an embodiment wherein the fermentable mixture is white or red grape juice the C6 aldehyde, a C6 alcohol or a combination thereof is introduced into the fermentable mixture by the introduction of vine leaves, preferably at least partially crushed vine leaves.

A further feature of the invention provides for the additional step of agitating the fermentable mixture prior to subjecting the fermentable mixture to fermentation to obtain a substantially uniform additive distribution in the fermentable mixture.

Still further features of the invention provide for the additional step of introducing a rehydrated yeast mixture to the fermentable mixture before subjecting the fermentable mixture to fermentation; and for the rehydrated yeast mixture to include active dry wine yeast and a yeast rehydration nutrient.

The invention extends to a fermented beverage produced by the method described above.

In accordance with a second aspect of the invention, there is provided a method for preparing a fermented beverage having a modulated aromatic profile, the method including: preparing a fermentable mixture; introducing a C6 aldehyde, C6 alcohol or a combination thereof into the fermentable mixture to obtain a predetermined concentration of the C6 aldehyde, C6 alcohol or the combination thereof in the fermentable mixture; and subjecting the fermentable mixture to fermentation.

Further features of this aspect of the invention provides for the C6 aldehyde to be (E)-2-hexenal; for the predetermined concentration of (E)-2-hexenal to be between about 0.5 and 3 mg/L; for the C6 alcohol to be (E)-2-hexenol; for the predetermined concentration of (E)-2-hexenol to be between about 7 and 15 mg/L; and for the C6 aldehyde, C6 alcohol or a combination thereof to be introduced into the fermentable mixture by the introduction of vine leaves.

This aspect of the invention extends to a fermented beverage produced by the method described above.

An embodiment of the invention will now be described, by way of example only, with reference to the accompanying drawings.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. For better understanding, the like elements have been designated by like reference numbers throughout the various accompanying figures. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

A method for preparing a fermented beverage having a modulated aromatic profile is provided. In particular, the method is for preparing a fermented beverage having a modulated or varied concentration of impact odorants or volatiles, more specifically varietal thiols such as 3MH and 3MHA. In effect, the intensity of fruity or tropical aromas experienced in consuming the fermented beverage is affected. Generally, the intensity of the fruity or tropical aromas is increased by the method.

The method for preparing a fermented beverage having a modulated aromatic profile includes preparing a fermentable mixture, introducing ammonium sulphide as an additive into the fermentable mixture to obtain a predetermined concentration of the ammonium sulphide in the fermentable mixture and then subjecting the fermentable mixture to fermentation.

The ammonium sulphide may be added to obtain a concentration of between about 1.5 and 50 mg/L, preferably between about 1.5 and 6.5 mg/L, more preferably between about 1.5 and 3 mg/L in the fermentable mixture or between about 3 and 50 mg/L, preferably between about 3 and 6.5 mg/L in the fermentable mixture. The predetermined concentration will be selected beforehand and the amount of ammonium sulphide to be added to the fermentable mixture will be calculated based on the volume of the fermentable mixture. A concentration may be selected based on the desired concentration of one or more varietal thiols in the fermented beverage produced according to the method.

An interval of between 1 hour and 24 hours, preferably about 24 hours, may be allowed after addition of ammonium sulphide to the fermentable mixture prior to subjecting the fermentable mixture to fermentation. This interval provides a period of contact time between the fermentable mixture and the ammonium sulphide.

It has been found that the addition of green leaf volatiles, in particular C6 aldehydes and alcohols further enhance the effect of ammonium sulphide on the aromatic profile of a fermented beverage when added to the fermentable mixture in combination with ammonium sulphide. C6 aldehydes, C6 alcohols or a combination thereof may thus be introduced into the fermentable mixture as a second additive together with ammonium sulphide as the first additive. The first and second additives may be added separately at different times or concurrently and in combination prior to fermentation. In particular, (E)-2-hexenal, (E)-2-hexenol or a combination thereof may be added to the fermentable mixture as a second additive prior to fermentation. The concentrations of (E)-2-hexenal or (E)-2-hexenol added to the fermentable mixture may depend on the type of fermentable mixture used and the amount of these types of compounds that may already be present or are normally present in the selected type of fermentable mixture. (E)-2-hexenal may be introduced into the fermentable mixture to obtain predetermined concentration of between about 0.5 and 3 mg/L. (E)-2-hexenol may be introduced into the fermentable mixture to obtain a predetermined concentration of between about 7 and 15 mg/L. (E)-2-hexenal and (E)-2-hexenol may be added to the fermentable mixture in combination in the same concentration ranges given above.

It has been found that adding C6 aldehydes, C6 alcohols or a combination thereof into the fermentable mixture (in the absence of ammonium sulphide) prior to subjecting the fermentable mixture to fermentation also modulates the aromatic profile of the fermented beverage, although to a lesser extent. These compounds may be derived from vine leaves or selected C6 aldehydes, C6 alcohols or combinations thereof, such as (E)-2-hexenal and (E)-2-hexenol whivch may be added to the fermentation mixture in predetermined concentrations such as the concentrations mentioned above.

The fermentable mixture may be fruit juice, must or wort. The fruit juice may be juice from white grapes or red grapes, particularly of the Vitis vinifera species. In a preferred embodiment the fruit juice is juice from Sauvignon Blanc grapes and preferably turbid or cloudy juice.

A combination of C6 aldehydes and alcohols which includes (E)-2-hexenal and/or (E)-2-hexenol may be introduced into the fermentable mixture through the introduction of vine leaves into the mixture. This is particularly convenient where the fermentable mixture is derived from white grape or red grape juice. Where vine leaves are so used it may be preferable that they be at least partially crushed or fragmented to aid in the more effective release of the green leaf volatiles such as C6 aldehydes and C6 alcohols, as well as C6 esters, contained therein. Any convenient method can be used to achieve this.

The fermentable mixture may also be agitated prior to subjecting it to fermentation. This may assist in obtaining a substantially uniform additive distribution, particularly where vine leaves are added. Any suitable form of agitation may be used, including mechanical agitation by means of an impeller or similar device.

A rehydrated yeast mixture may be added to the fermentable mixture before subjecting the fermentable mixture to fermentation. This may occur in any suitable manner and the amount added may be calculated based on known dosing requirements. The rehydrated yeast mixture may include active dry wine yeast and a yeast rehydration nutrient.

There is further provided a fermented beverage or drink produced by the method described above. The fermented beverage may be a wine, but it can include other fermented beverages including those made from fruit juice such as ciders.

Figure 1:
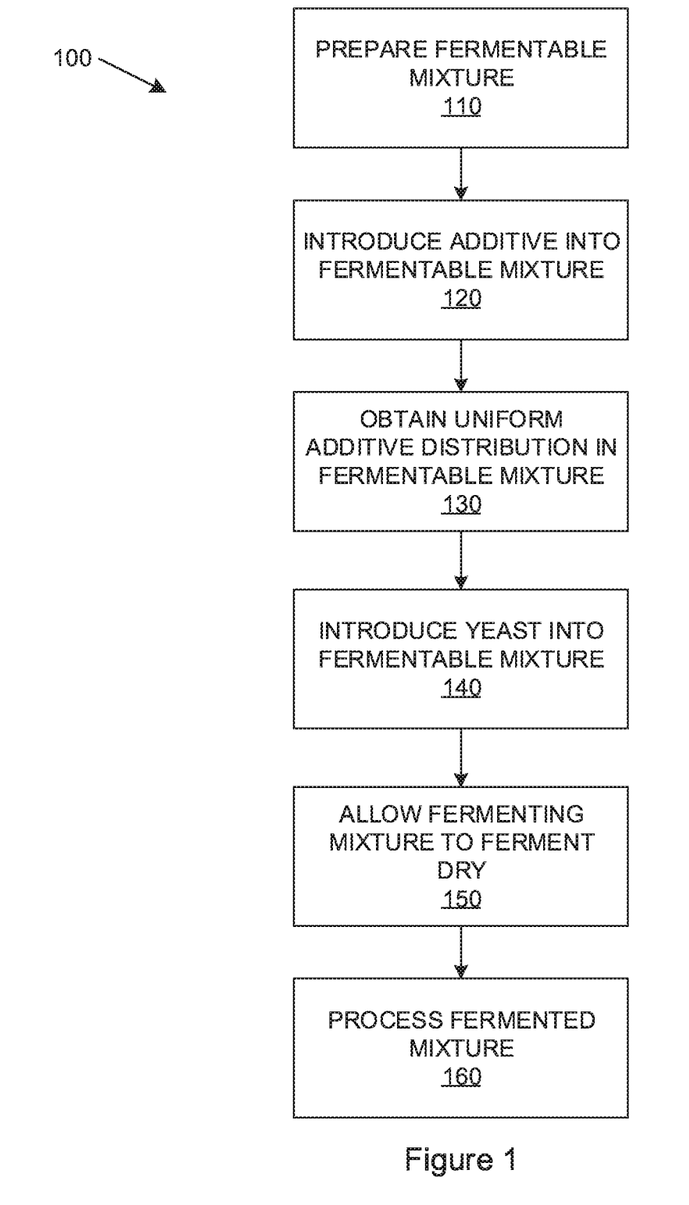
FIG. 1 is a flow diagram illustrating a method of preparing a fermented beverage having a modulated aromatic profile.

FIG. 1 illustrates a flow diagram of a method (100) for producing a fermented beverage having a modulated aromatic profile according to an embodiment of the invention. The method (100) includes the step of preparing (110) a fermentable mixture. In this embodiment, the fermentable mixture is juice extracted from Vitis vinifera species of grapes by means of pressing. More specifically, the fermentable mixture is juice extracted from Sauvignon Blanc grapes, which is a lower classification of the Vitis vinifera species. The juice is maintained at a nominal temperature of about 15° C. Then, an additive is introduced (120) into the juice. In the present embodiment, the additive is an aqueous solution of ammonium sulphide $(NH_4)_2S$. The quantity of $(NH_4)_2S$ additive introduced into the juice is measured so as to obtain a predetermined concentration thereof in the juice. In this embodiment, the predetermined concentration is between about 1.5 mg/L and 50 mg/L. The fermentable mixture is lightly agitated (130) to obtain a uniform additive distribution therein.

Next, rehydrated dry wine yeast is introduced (140) into the fermentable mixture. A person skilled in the relevant art will be aware of the manners in which this may be performed. The fermentable mixture is allowed to ferment (150) dry. Thereafter, the fermented mixture is processed further (160), for example the fermented mixture is filtered and bottled, as may be appropriate or desired by the artisan.

Experimental Section

FIGS. 2 to 5 show the results of a first experiment (experiment 1) and are bar graphs that depict the concentrations of varietal thiols, 3MH and 3MHA, in the fermented mixture obtained from carrying out the method (100) of FIG. 1 on four different types of fermentable mixtures containing different concentrations of ammonium sulphide. The experiment was performed using Sauvignon Blanc grapes from the 2015 harvest that were obtained from four independent wine farms in the Western Cape Province of South Africa, each with substantially differing terroir. The grapes from each farm were pressed to obtain the juice intended for fermentation, thereby preparing the fermentable mixture. For each of the four mixtures, three separate sets of experiments were performed.

The first experiment for each mixture was a control group to which no additive was introduced, thus the fermentable mixture had a $(NH_4)_2S$ concentration of 0 mg/L. For the second experiment an aqueous solution of $(NH_4)_2S$ was introduced to each fermentable mixture such as to obtain a concentration of 3.1 mg/L. And lastly, for the third experiment, an aqueous solution of $(NH_4)_2S$ was introduced to each fermentable mixture so as to obtain a concentration of 6.2 mg/L. These sets will subsequently be referred to as the control group samples, the 3.1 mg/L samples and the 6.2 mg/L samples respectively.

The experiments were performed in triplicate in order to pre-empt a possible anomalous result set. A combination of 700 mL, 2 L and 4 L samples were used. Each additive-containing sample was lightly stirred or agitated subsequent to the introduction of the additive so as to obtain a substantially uniform distribution throughout the mixture. Thereafter, rehydrated yeast was introduced to each sample. In this experiment, "VIN7", a Saccharomyces cerevisiae yeast from Anchor Wine Yeast™, was used and rehydrated using "Go-Ferm Protect Evolution" from Lallemand™. After three days of inoculation, "FERMAID K", also from Lallemand™, was introduced to each sample as a yeast nutrient.

The samples of fermenting mixture were allowed to ferment dry, after which the samples were sent for laboratory analysis to obtain readings of the 3MH and 3MHA concentrations contained in the samples. The analyses were performed using Ultra Performance Liquid Chromatography (UPLC).

Figure 2:
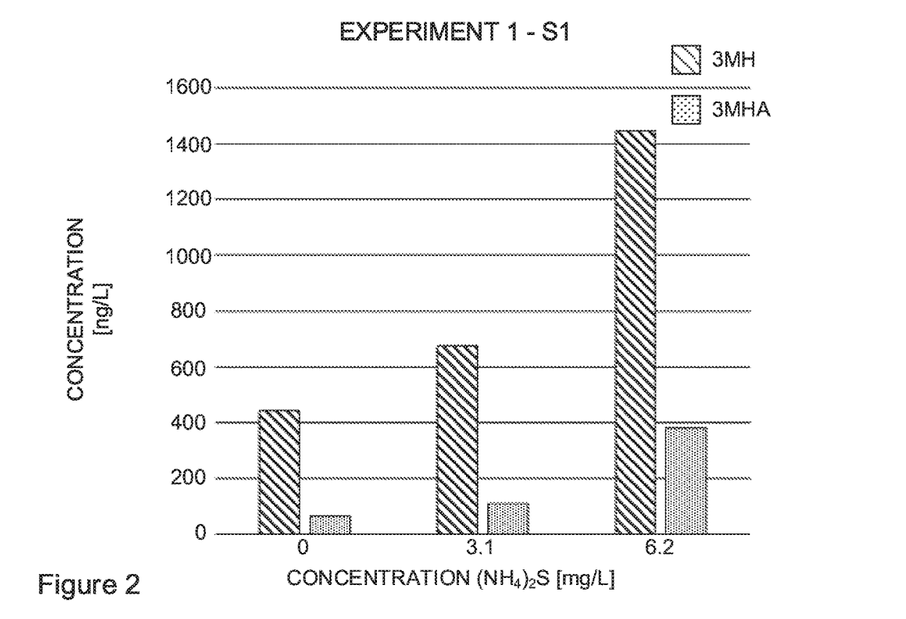
FIGS. 2 to 5 relate to a first experiment and are bar graphs that depict the concentrations of varietal thiols, 3MH and 3MHA, in the fermented mixture after carrying out the method of FIG. 1 on four different types of fermentable mixtures, labelled S1, S2, S3 and S4, to which 0, 3.1 and 6.2 mg/L of ammonium sulphide have been added prior to fermentation.

FIG. 2 shows the 3MH and 3MHA concentrations for the control group samples, the 3.1 mg/L samples and the 6.2 mg/L samples respectively for the Sauvignon Blanc from the first wine farm (S1). The mean value of the three samples for each set was calculated. The control group samples yielded average 3MH and 3MHA concentrations of 442 nanograms per litre (ng/L) and 65 ng/L respectively. The 3.1 mg/L samples yielded average 3MH and 3MHA concentrations 675 ng/L and 109 ng/L respectively. This shows a 53% increase in the concentration of 3MH and a 70% increase in the concentration of 3MHA respectively compared to the control group. The 6.2 mg/L samples yielded average 3MH and 3MHA concentrations of 1446 ng/L and 381 ng/L respectively. This is a 228% increase in the concentration of 3MH and 490% increase in the concentration of 3MHA respectively compared to the control group.

Figure 3:
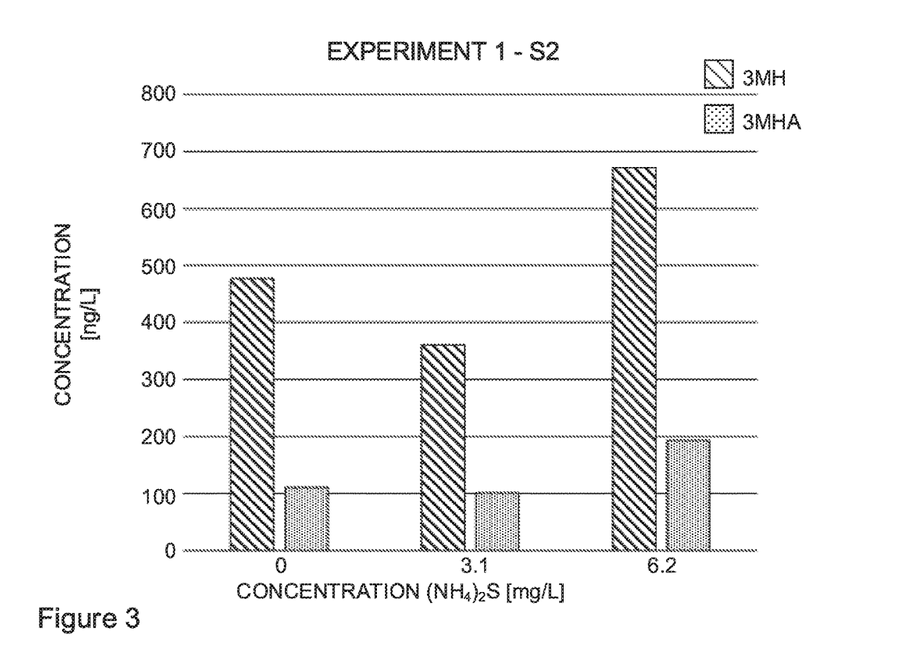

FIG. 3 shows the corresponding results for the Sauvignon Blanc from the second wine farm (S2). The mean value of the three samples for each set was again calculated. The control group samples yielded average 3MH and 3MHA concentrations of 477 ng/L and 110 ng/L respectively. The 3.1 mg/L samples yielded average 3MH and 3MHA concentrations of 361 ng/L and 101 ng/L respectively and the 6.2 mg/L samples yielded average 3MH and 3MHA concentrations 672 ng/L and 193 ng/L respectively. Although the 3.1 mg/L samples show decreased concentrations, the 6.2 mg/L samples again show increases in concentration of 41% and 75% for 3MH and 3MHA respectively compared to the control group.

Figure 4:
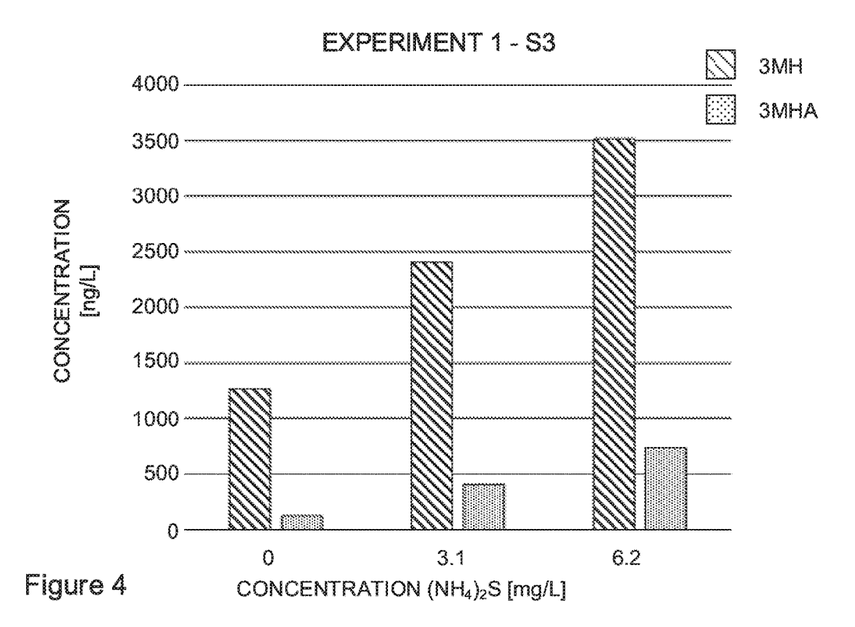

FIG. 4 shows the corresponding results for the Sauvignon Blanc from the third wine farm (S3). The mean value of the three samples for each set was again calculated. The control group samples yielded average 3MH and 3MHA concentrations of 1270 ng/L and 124 ng/L respectively. The 3.1 mg/L samples yielded average 3MH and 3MHA concentrations of 2407 ng/L and 407 ng/L respectively and the 6.2 mg/L samples yielded average 3MH and 3MHA concentrations of 3516 ng/L and 736 ng/L respectively. This is a 90% increase in the concentration of 3MH and 229% increase in the concentration of 3MHA respectively and an increase of 176% in the concentration of 3MH and 495% of 3MHA respectively, both in comparison to the control group.

Figure 5:
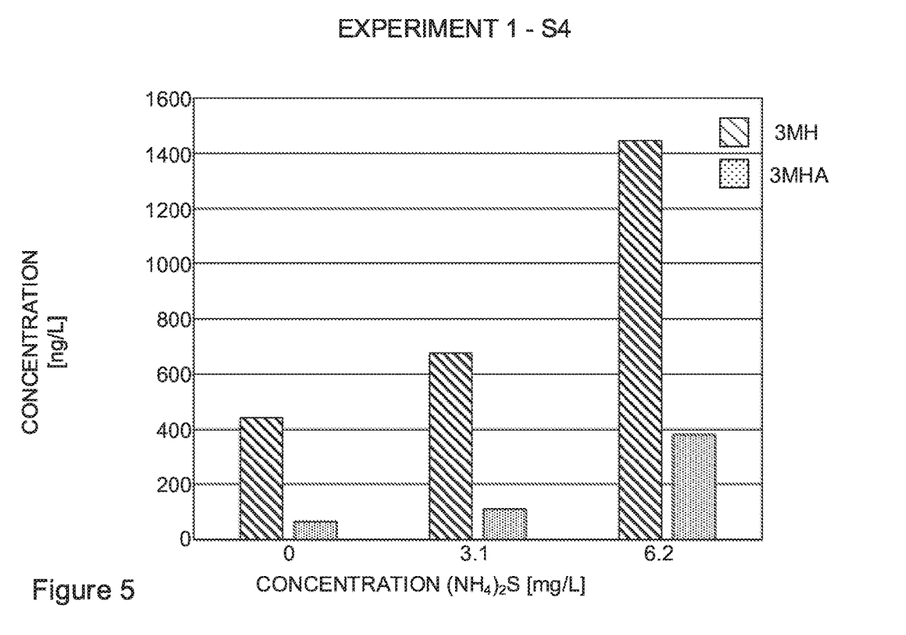

FIG. 5 shows the corresponding results for the Sauvignon Blanc from the fourth wine farm (S4). The mean value of the three samples for each set was again calculated. The control group samples yielded average 3MH and 3MHA concentrations of 442 ng/L and 65 ng/L respectively. The 3.1 mg/L samples yielded average 3MH and 3MHA concentrations of 675 ng/L and 109 ng/L respectively and the 6.2 mg/L samples yielded average 3MH and 3MHA concentrations of 1447 ng/L and 381 ng/L respectively. This is a 53% increase in the concentration of 3MH and 69% increase in the concentration of 3MHA respectively, and an increase of 228% in the concentration of 3MH and 490% of 3MHA respectively, both in comparison to the control group.

The results from the initial experiment therefore indicate that the method described above does modulate the 3MH and 3MHA concentrations in the fermented beverage, in this case Sauvignon Blanc white wine, and therefore also modulates the aromatic profile thereof. More specifically, they indicate that an increased concentration $(NH_4)_2S$ in the fermentable mixture generally results in increased concentrations of 3MH and 3MHA in the resulting fermented beverage.

A subsequent experiment (experiment 2) was performed using grapes from wine farms S1, S3 and S4 to investigate the above-mentioned causal relationship and to confirm whether an increased concentration of $(NH_4)_2S$ in the fermentable mixture generally results in increased concentrations of 3MH and 3MHA in the resulting fermented beverage. The results thereof are shown in Table 1 below with the corresponding graphs shown in FIGS. 6 to 8.

TABLE 1

Figure 6:
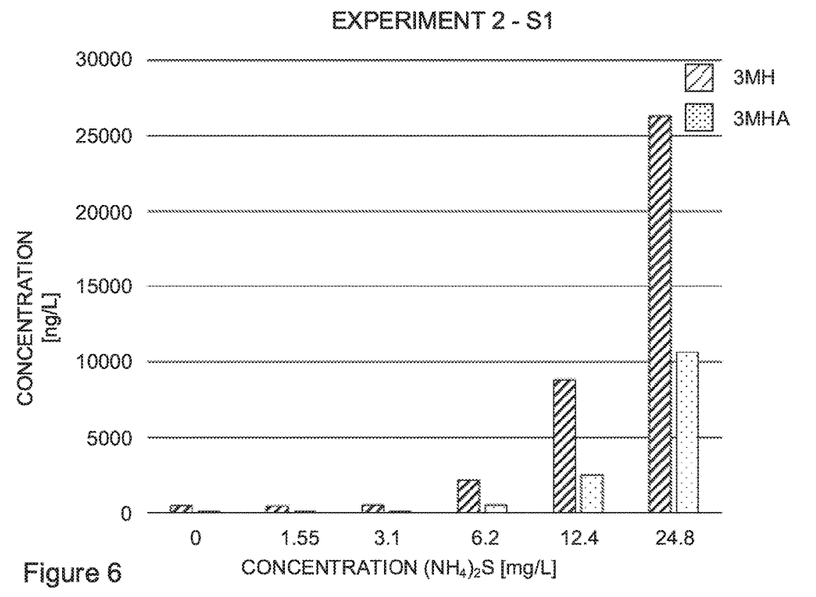
FIGS. 6 to 8 relate to a second experiment and are bar graphs that show the concentrations of 3MH and 3MHA in fermented beverages following fermentation of fermentable mixtures S1, S3 and S4 containing 0, 1.5, 3.1, 6.2, 12.4, 24.8 mg/L ammonium sulphide, respectively.
Figure 7:
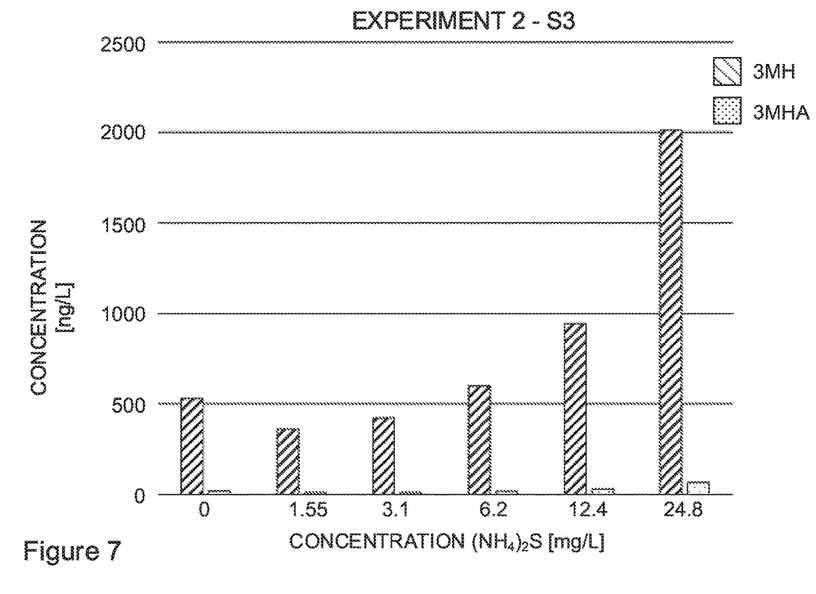
Figure 8:
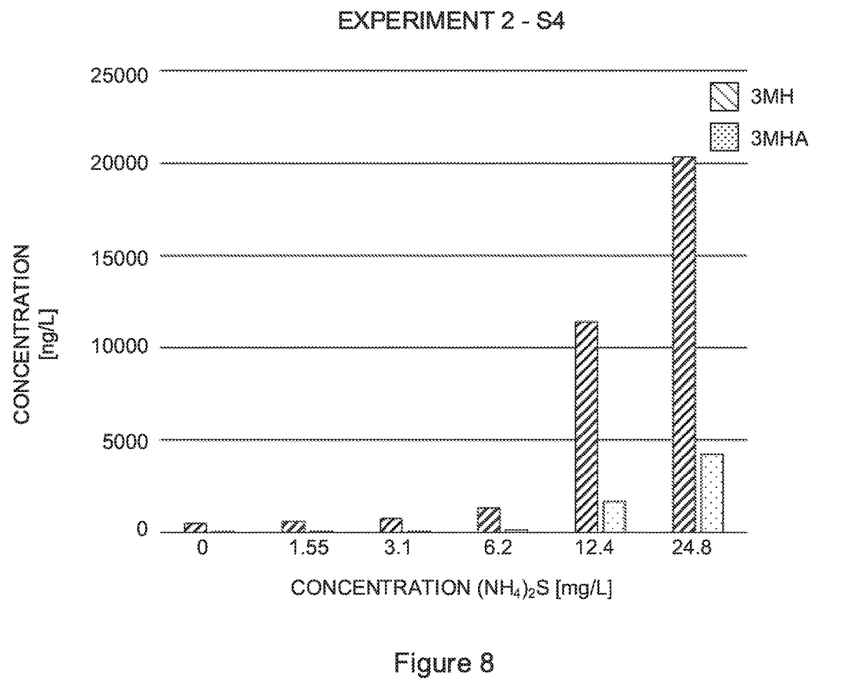

Concentrations of 3MH and 3MHA with increasing concentrations of $(NH_4)_2S$ in mixture

| Concentration $(NH_4)_2S$ [mg/L] | Concentration 3MH [ng/L] | Concentration 3MHA [ng/L] |
|---|---|---|
| S1 (FIG. 6) | | |
| 0 | 474.60 | 63.8 |
| 1.5 | 439.31 | 54.86 |
| 3.1 | 518.92 | 80.335 |
| 6.2 | 2194.77 | 510.5 |
| 12.4 | 8831.92 | 2525.01 |
| 24.8 | 26295.00 | 10647.33 |
| S3 (FIG. 7) | | |
| 0 | 528.64 | 19.43 |
| 1.5 | 359.43 | 9.78 |
| 3.1 | 421.51 | 9.87 |
| 6.2 | 598.77 | 17.30 |
| 12.4 | 945.02 | 29.30 |
| 24.8 | 2010.82 | 67.03 |
| S4 (FIG. 8) | | |
| 0 | 465.59 | 28.4 |
| 1.5 | 586.60 | 52.2 |
| 3.1 | 734.76 | 51.9 |
| 6.2 | 1298.87 | 127.7 |
| 12.4 | 11396.98 | 1646.3 |
| 24.8 | 20342.10 | 4255.9 |

The results from this experiment clearly indicate, and thus confirm, that increased concentrations of $(NH_4)_2S$ in a fermentable mixture generally result in increased concentrations of 3MH and 3MHA in the resulting fermented beverage. The results for S1, shown in FIG. 6, show increases in 3MH of up to 5400% and increases in 3MHA of up to 16600% compared to the control group.

It should be noted that other ammonium compounds, such as $(NH_4)_2SO_4$ and $(NH_4)_2SO_3$ are known to be used as a source of nitrogen for yeast assimilation during the fermentation of wine. These ammonium compounds are typically introduced to the fermentable mixture in concentrations of about between 100 mg/L and 200 mg/L. Using these ammonium compounds in the much lower concentrations, as in the experiments of the present disclosure (between about 1.5mg/L and 6.2 mg/L), would not serve as sufficient nitrogen sources. Conversely, using $(NH_4)_2S$ in the much higher concentrations (that of the other ammonium compounds that are used for as nitrogen sources), would, at the very least, result in a wine with a high degree of undesirable or reductive aromas, including that of rotten eggs.

Figure 9:
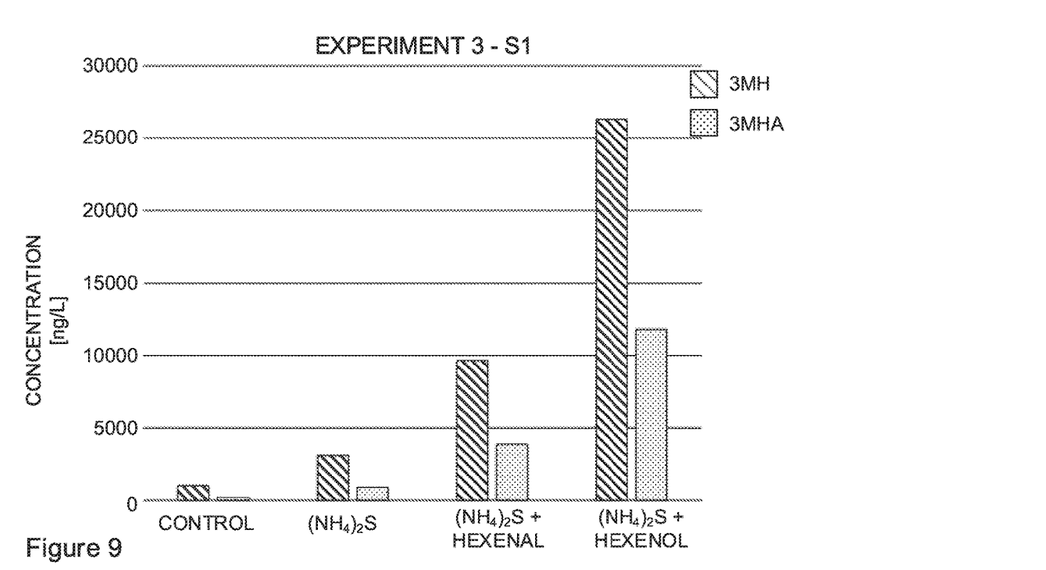
FIGS. 9 to 11 relate to a third experiment and are bar graphs that show the concentrations of 3MH and 3MHA in fermented beverages following fermentation of fermentable mixtures S1, S3 and S4 that contained zero additives (control), 6.2 mg/L ammonium sulphide, 6.2 mg/L ammonium sulphide plus 1.5 mg/L (E)-2-hexanal and 6.2 mg/L ammonium sulphide plus 10 mg/L (E)-2-hexenol.
Figure 10:
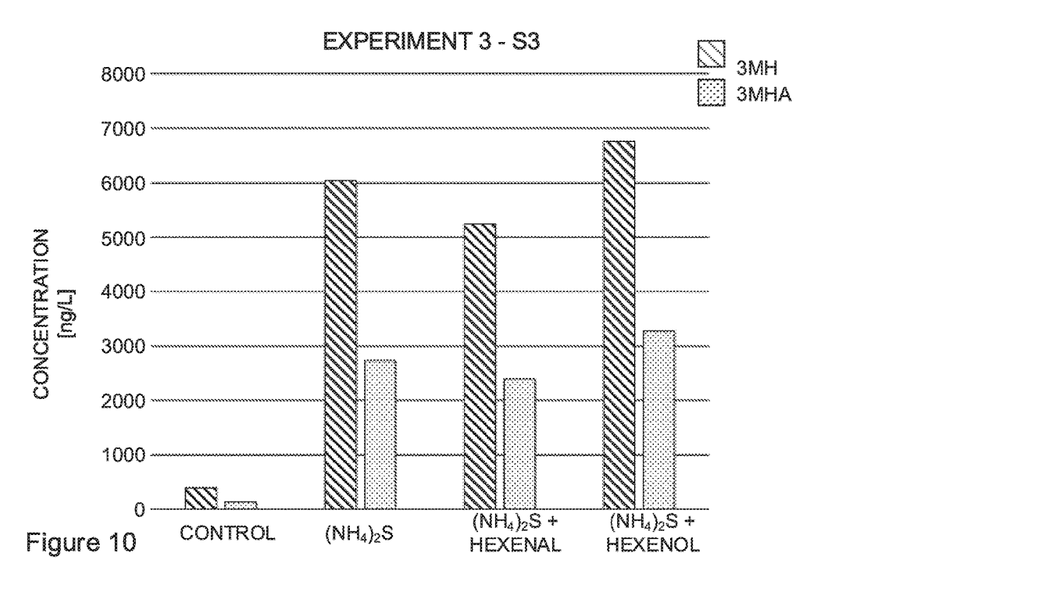
Figure 11:
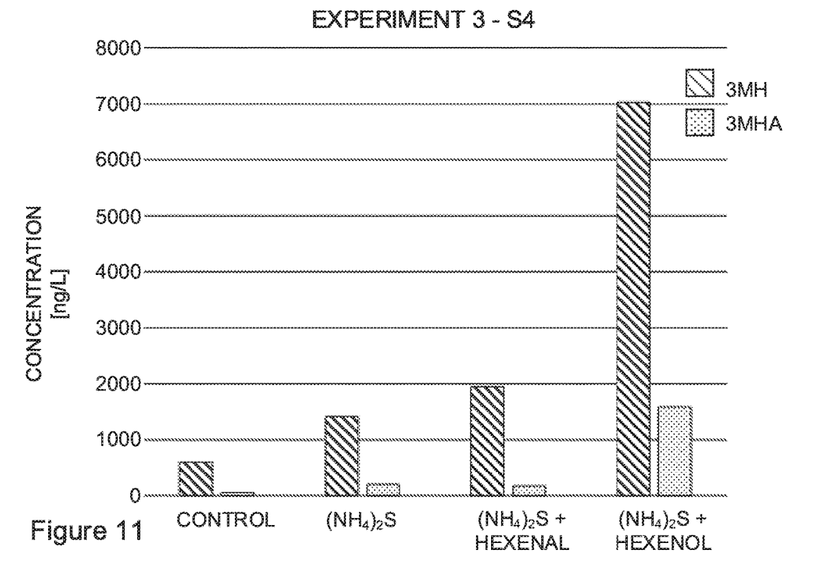

A further experiment (experiment 3) was conducted with grapes from wine farms S1, S3 and S4 wherein a second or additional additive or precursor was introduced into the fermentable mixture prior to fermentation. The experiment was performed with a control group, wherein no precursor additive was introduced, a first group wherein only $(NH_4)_2S$ was introduced in a concentration of 6.2 mg/L, a second group further including (E)-2-hexenal in a concentration of 1.5 mg/L and a third group wherein the (E)-2-hexenal was substituted for (E)-2-hexenol in concentrations of 10 mg/L. In all of groups 1, 2 and 3, therefore, $(NH_4)_2S$ was present in the fermentable mixture.

The results of this experiment are shown in Table 2 below with the corresponding graphs shown in FIGS. 9 to 11. These results indicate that the addition of (E)-2-hexenal (referred to as "hexenal" in FIGS. 9 to 11) and (E)-2-hexenol (referred to as "hexenol" in FIGS. 9 to 11) to the fermentable mixture did in fact modulate the aromatic profile of the fermented beverage, in this embodiment wine. Furthermore, in at least one experiment, the further addition of both (E)-2-hexenal and (E)-2-hexenol resulted in increased 3MH and 3MHA concentrations (2500% and 5500% increases respectively). This indicates that it had a synergistic effect with ammonium sulphide in increasing the concentration of varietal thiols, thereby increasing the intensity of fruity aromas in the wine.

TABLE 2

Concentrations of 3MH and 3MHA with selected precursors

| Concentration Precursor [mg/L] | Concentration 3MH [ng/L] | Concentration 3MHA [ng/L] |
|---|---|---|
| S1 (FIG. 9) | | |
| 0 | 993.75 | 210.09 |
| 6.2 $(NH_4)_2S$ | 3094.16 | 899.33 |
| 6.2 $(NH_4)_2S$ + 1.5 (E)-2-hexenal | 9629.17 | 3848.16 |
| 6.2 $(NH_4)_2S$ + 10 (E)-2-hexenol | 26284.02 | 11804.22 |
| S3 (FIG. 10) | | |
| 0 | 391.04 | 135.49 |
| 6.2 $(NH_4)_2S$ | 6039.16 | 2729.88 |
| 6.2 $(NH_4)_2S$ + 1.5 (E)-2-hexenal | 5246.29 | 2394.64 |
| 6.2 $(NH_4)_2S$ + 10 (E)-2-hexenol | 6762.49 | 3276.49 |
| S4 (FIG. 11) | | |
| 0 | 604.27 | 58.0 |
| 6.2 $(NH_4)_2S$ | 1409.59 | 204.0 |
| 6.2 $(NH_4)_2S$ + 1.5 (E)-2-hexenal | 1939.68 | 180.1 |
| 6.2 $(NH_4)_2S$ + 10 (E)-2-hexenol | 7034.87 | 1584.1 |

The experiment above was further extended (experiment 4) by utilising the leaves from the vine of the particular grape. This subsequent experiment served to investigate whether at least similar effects could be observed with the use of naturally occurring C6 aldehydes and alcohols such as (E)-2-hexenal and (E)-2-hexenol derived from vine leaves compared to the results where these compounds were introduced artificially as additives.

This experiment (experiment 4) was performed with a first group in which only $(NH_4)_2S$ was introduced in a concentration of 6.2 mg/L, a second group in which leaves from the particular vine were introduced at a ratio of 10 grams per litre (g/L), and a third group in which $(NH_4)_2S$ and leaves were introduced in combination, using the same concentrations and ratios. Each group was repeated allowing varying contact times with the skins of the grapes: no skin contact, 6 hours of skin contact, and 12 hours of skin contact.

Figure 12:
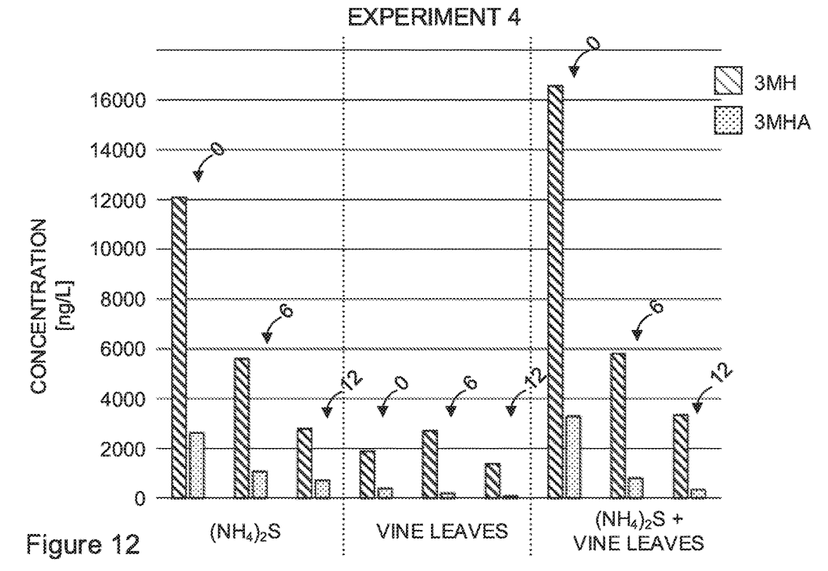
FIG. 12 relates to a fourth experiment and is a bar graph that shows the concentrations of 3MH and 3MHA in fermented beverages following fermentation of fermentable mixtures with only ammonium sulphide, only vine leaves and ammonium sulphide plus vine leaves.

The results of this experiment (experiment 4) are shown in Table 3 below with the corresponding a graph shown in FIG. 12.

TABLE 3

Concentrations of 3MH and 3MHA with selected precursors

| Precursor Concentration | Skin Contact [Hrs] | Concentration 3MH [ng/L] | Concentration 3MHA [ng/L] |
|---|---|---|---|
| $(NH_4)_2S$ [6.2 mg/L] | 0 | 12082 | 2617.40 |
| | 6 | 5589 | 1052.36 |
| | 12 | 2793 | 715.81 |
| Leaves [10 g/L] | 0 | 1894 | 383.97 |
| | 6 | 2706 | 166.08 |
| | 12 | 1368 | 52.91 |
| $(NH_4)_2S$ [6.2 mg/L] + Leaves [10 g/L] | 0 | 16554 | 3296.83 |
| | 6 | 5815 | 784.95 |
| | 12 | 3345 | 325.92 |

These results indicate that similar effects can be observed when using vine leaves as a source of C6 aldehydes and C6 alcohols including (E)-2-hexenal and (E)-2-hexenol. At least one result indicated a dramatic increase in the concentration 3MH and 3MHA in the fermented beverage when used in concert with $(NH_4)_2S$ in the method described above.

This result is surprising as leaves are generally thought to have an undesirable effect on the wine and are usually removed prior to pressing.

In order to ascertain the perceived aromatic components to the user, a sensory experiment (experiment 5) was performed. Ten tasters were trained to identify aromatic descriptors such as guava, banana candy, yellow apple, tomato leaf and cooked vegetables. The tasters were then asked to rate the intensity of each of these descriptors in four different wines that were produced using the method described above and using varying precursors as described above. The samples were blindly presented to the tasters and consisted of a control group to which no precursors were introduced, a first group to which $(NH_4)_2S$ was introduced in a concentration of 3.1 mg/L, a second group to which a combination of $(NH_4)_2S$ and (E)-2-hexenol was introduced in concentrations of 3.1 and 10 mg/L respectively, and a third group to which only (E)-2-hexenol was introduced in a concentration of about 10 mg/L.

Figure 13:
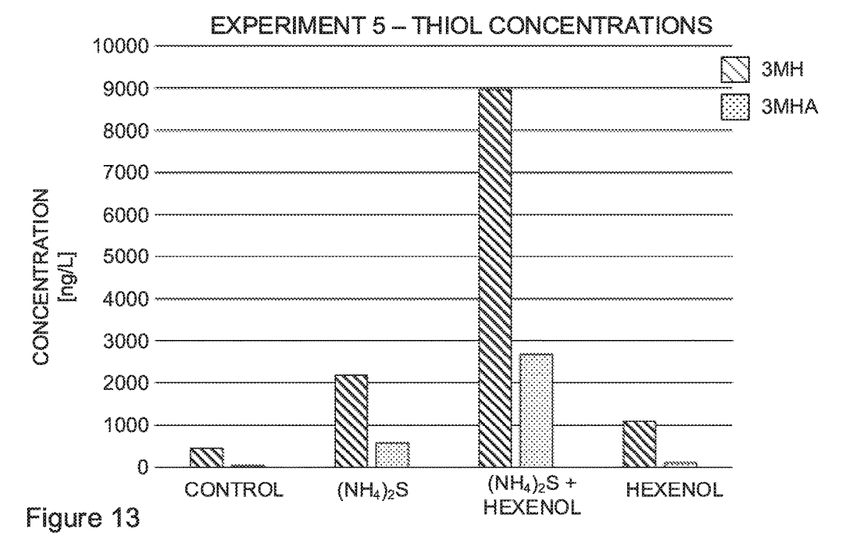
FIGS. 13 relates to a fifth experiment and is a bar graph that shows the concentration of 3MH and 3MHA in fermented beverages following fermentation of fermentable mixtures that contained zero additives (control), 3.1 mg/L ammonium sulphide, 3.1 mg/L ammonium sulphide plus 10 mg/L (E)-2-hexanol and only 10 mg/L (E)-2-hexenol.
Figure 14:
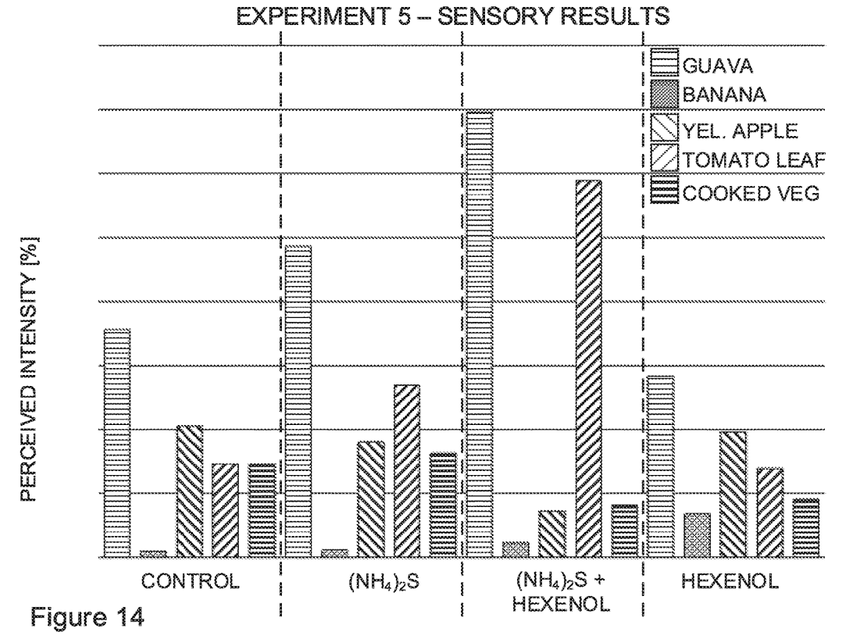
FIG. 14 relates to the fifth experiment and is a bar graph that shows the sensory results of the perceived aromatic components of the fermented beverage samples of FIG. 13.

FIG. 13 shows the concentration 3MH and 3MHA in the resulting wine samples. FIG. 14 indicates an average rating out of 100 for each sample as indicated by the tasters. The tasters rated the perceived intensity of each of the aromatic descriptors, consisting of guava, banana candy, yellow apple, tomato leaf and cooked vegetables as a percentage. The results indicate that there is a correlation between the concentration 3MH in the wine and the perceived aromatic profile. This is most evident from the perceived guava intensity, which follows a similar trend to the concentration of 3MH in the relevant sample.

In the experiments described above, the addition of $(NH_4)_2S$ was followed immediately or shortly thereafter by inoculation and thus subjecting the fermentable mixture to fermentation. Further experiments were performed to investigate whether an increased contact time between the $(NH_4)_2S$ additive and the fermentable mixture before fermentation had an influence on the 3MH and 3MHA concentrations in the resultant wine.

Furthermore, grape juice is often clarified prior to alcoholic fermentation. Reasons for this may include the removal of unwanted skin particles, stem particles, flesh residue, seeds, dust, and unwanted yeasts and bacteria which originate from the vineyard. The cloudiness of the juice is referred to as the turbidity thereof. The degree of juice clarity or non-turbidity required is a parameter considered by the winemaker as excessive clarification may also lead to undesirable fermentation results. A natural way to clarify the juice is to allow the particles causing the turbidity to settle to the bottom of the liquid.

Figure 15:
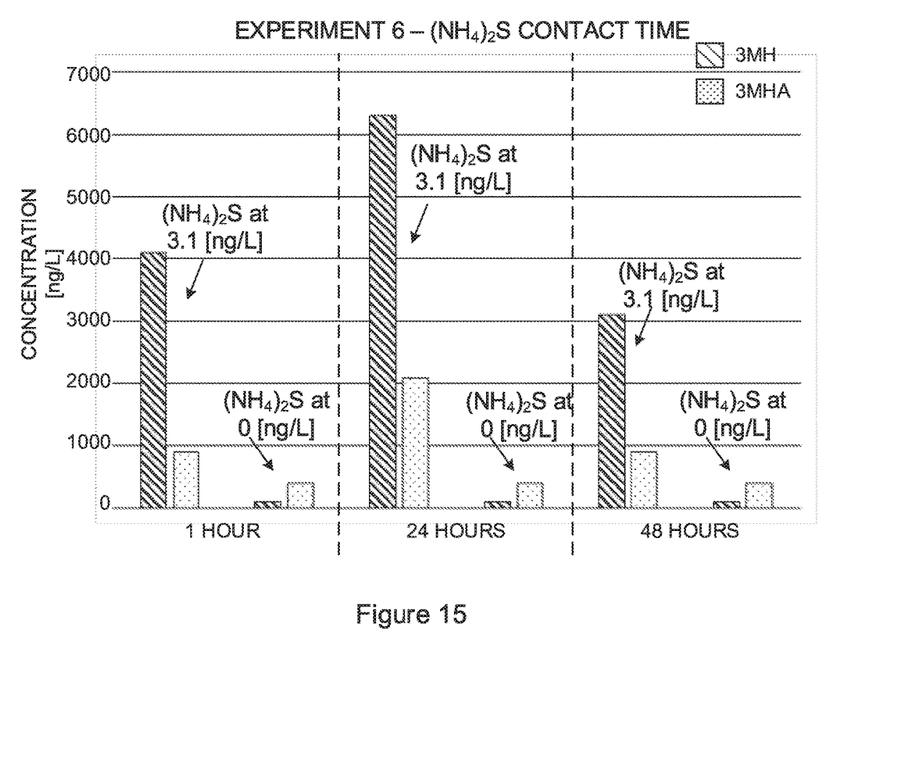
FIG. 15 relates to a sixth experiment and is a bar graph that shows the concentration of 3MH and 3MHA in fermented beverages following fermentation of fermentable mixtures that contain either zero or 3.1 mg/L ammonium sulphide and in which contact times of 1 hour, 24 hours and 48 hours, respectively, were allowed before fermentation.

FIG. 15 shows experimental results from a sixth experiment performed using clear (substantially non-turbid) Sauvignon Blanc juice in which the fermentable mixture was allowed a contact time with $(NH_4)_2S$ of 1 hour, 24 hours and 48 hours respectively before subjecting the mixture to fermentation. Results of samples having had no $(NH_4)_2S$ additive are provided as control samples. The data from these experiments are shown below in Table 4.

TABLE 4

Concentrations of 3MH and 3MHA after varying contact time with $(NH_4)_2S$

| Concentration Precursor [mg/L] | Contact Time [Hrs] | Concentration 3MHA [ng/L] | Concentration 3MH [ng/L] |
|---|---|---|---|
| $(NH_4)_2S$ [3.1 mg/L] | 1 | 845.6 | 4262.6 |
| | 24 | 2218.2 | 6441.9 |
| | 48 | 831.8 | 3240.5 |
| Zero (Control Sample) | 1 | 446.7 | 167.6 |
| | 24 | 461.9 | 207.0 |
| | 48 | 453.3 | 224.6 |

From the data shown in Table 4 and FIG. 15 it may be observed that a 24 hour contact time between $(NH_4)_2S$ and the fermentable mixture before inoculation produced the greatest concentrations of 3MH and 3MHA concentrations in the resultant wine.

Next, the effect of varying turbidity of the fermentable mixture in combination with a 24 hour contact time between the fermentable mixture and $(NH_4)_2S$ on the 3MH and 3MHA concentrations in the resultant wine was investigated in a seventh experiment.

Figure 16:
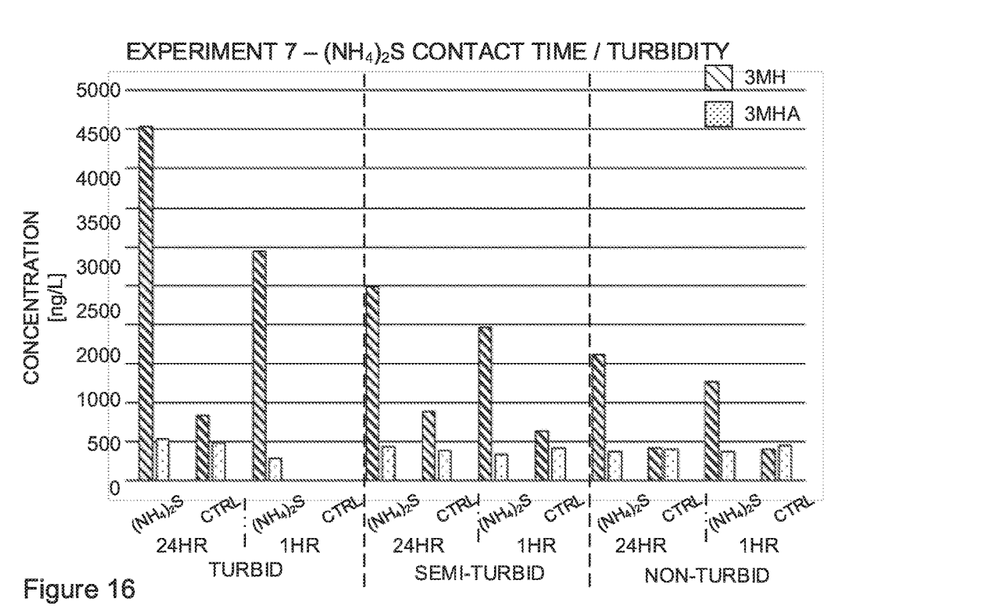
FIGS. 16 to 17 relate to a seventh experiment and are bar graphs showing the concentration of 3MH and 3MHA in fermented beverages following fermentation of fermentable mixtures that are turbid, semi-turbid or non-turbid with or without 3.1 mg/L ammonium sulphide and allowing for contact times of either 1 or 24 hours.
Figure 17:
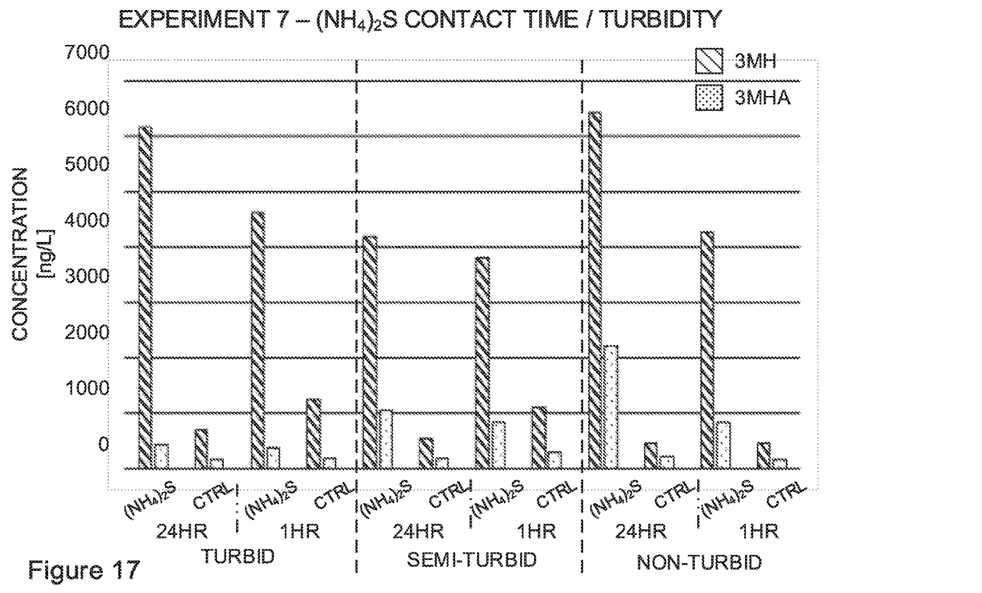

Experiments were performed using Sauvignon Blanc juice from two different farms. In each case, a turbid juice, a semi-turbid juice and a substantially non-turbid juice were used, each of which were allowed 1 hour and 24 hours of contact with $(NH_4)_2S$ respectively. Samples to which no $(NH_4)_2S$ was added were used as control samples. Table 5 shows the data from this experiment using the juice from one farm and Table 6 shows the data from this experiment using the juice from the other of the two farms. FIGS. 16 and 17 show graphs corresponding to the data in Table 5 and Table 6 respectively.

TABLE 5

Concentrations of 3MH and 3MHA after varying contact time with $(NH_4)_2S$ and varying turbidity using juice from one farm

| Clarity | Contact Time | Concentration $(NH_4)_2S$ [mg/L] | Concentration 3MH [ng/L] | Concentration 3MHA [ng/L] |
|---|---|---|---|---|
| Turbid | 24 h | 3.1 | 4533.374 | 543.763 |
| | | 0 | 842.618 | 479.339 |
| | 1 h | 3.1 | 2948.29 | 286.629 |
| | | 0 | — | — |
| Intermediate (semi-turbid) | 24 h | 3.1 | 2474.362 | 435.466 |
| | | 0 | 879.079 | 389.835 |
| | 1 h | 3.1 | 1971 | 331 |
| | | 0 | 640.2 | 418 |
| Non-turbid | 24 h | 3.1 | 1613.365 | 363.524 |
| | | 0 | 422.454 | 409.709 |
| | 1 h | 3.1 | 1270.531 | 376.46 |
| | | 0 | 408.883 | 452.567 |

TABLE 1

Concentrations of 3MH and 3MHA after varying contact time with $(NH_4)_2S$ and varying turbidity using juice from one farm

| Clarity | Contact Time | Concentration $(NH_4)_2S$ [mg/L] | Concentration 3MH [ng/L] | Concentration 3MHA [ng/L] |
|---|---|---|---|---|
| Turbid | 24 h | 3.1 | 6155.184 | 422.374 |
| | | 0 | 696.0341 | 145.48 |
| | 1 h | 3.1 | 4619.775 | 387.234 |
| | | 0 | 1238.04 | 179.571 |
| Intermediate (semi-turbid) | 24 h | 3.1 | 4200.93 | 1049.752 |
| | | 0 | 528.5764 | 174.983 |
| | 1 h | 3.1 | 3802.806 | 825.972 |
| | | 0 | 1102.073 | 287.772 |
| Non-turbid | 24 h | 3.1 | 6441.892 | 2218.215 |
| | | 0 | 461.9239 | 206.986 |
| | 1 h | 3.1 | 4262.64 | 845.671 |
| | | 0 | 446.7337 | 167.568 |

The results from Table 5 show the greatest concentrations of 3MH and 3MHA in the resultant wine in the case of the turbid juice and the least in the substantially non-turbid juice. The results using the juice from the second of these farms seem to be inconclusive. In both cases, however, a distinctly increased concentration in the resultant 3MH and 3MHA may be observed in the cases where 24 hours of contact time was allowed $(NH_4)_2S$ before inoculation.

The present invention therefore provides a method for preparing a fermented beverage which results in a fermented beverage of which the fruity or tropical aromas have greater intensity in comparison to control samples due to the fact that it contains a higher concentration of varietal thiols such as 3MH and 3MHA. It will be understood by those skilled in the art that the concentration of ammonium sulphide added to the fermentable mixture may vary depending on the extent to which the artisan wishes to modulate the aromatic profile of the fermented beverage, i.e. according to the desired concentration of varietal thiols in the fermented beverage. The contact time of the fermentable mixture with ammonium sulphide may also be varied to obtain a preselected concentration of varietal thiols in the fermented beverage. When a relatively high concentration thereof is desired, the fermented beverage will be allowed a contact time of about 24 hours. Further ways in which the concentration of varietal thiols in the fermented beverage may be increased, include the addition of C6 aldehydes, C6 alcohols or combinations thereof to the fermentable mixture together with the ammonium sulphide, prior to fermentation. These may be naturally occurring and derived from vine leaves or even grape skins, or specific C6 aldehydes and C6 alcohols such as (E)-2-hexanol and (E)-2-hexenol may be used. Those skilled in the art would select a concentration of C6 aldehydes, C6 alcohols or combinations thereof based on the desired concentration of varietal thiols in the end product, without substantially exceeding the amounts of these types of compounds that may normally be present or consumed in a particular type of fermentable mixture such as fruit juice.

Throughout the specification unless the contents requires otherwise the word 'comprise' or variations such as 'comprises' or 'comprising' will be understood to imply the inclusion of a stated integer or group of integers but not the exclusion of any other integer or group of integers.

We claim:

1. A method for preparing a fermented beverage having a modulated aromatic profile, the method including:
   preparing a fermentable mixture;
   introducing ammonium sulphide into the fermentable mixture to obtain a predetermined concentration of ammonium sulphide in the fermentable mixture; and
   subjecting the fermentable mixture to fermentation.

2. The method as claimed in claim 1, wherein an aqueous solution of ammonium sulphide is introduced into the fermentable mixture and wherein the predetermined concentration is between about 1.5 and 50 mg/L.

3. The method as claimed in claim 2, wherein the predetermined concentration is between about 1.5 and 6.5 mg/L.

4. The method as claimed in claim 1, wherein the method further includes the additional step of allowing between 1 hour and 24 hours of contact time between the fermentable mixture and the ammonium sulphide prior to subjecting the fermentable mixture to fermentation.

5. The method as claimed in claim 1, wherein a C6 aldehyde, a C6 alcohol or a combination thereof is introduced into the fermentable mixture before subjecting the fermentable mixture to fermentation.

6. The method as claimed in claim 5, wherein the C6 aldehyde is (E)-2-hexenal.

7. The method as claimed in claim 6, wherein the (E)-2-hexenal is introduced into the fermentable mixture to obtain a concentration of between about 0.5 and 3 mg/L thereof in the fermentable mixture.

8. The method as claimed in claim 5, wherein the C6 alcohol is (E)-2-hexenol.

9. The method as claimed in claim 8, wherein the (E)-2-hexenol is introduced into the fermentable mixture to obtain a concentration of between about 7 and 15 mg/L thereof in the fermentable mixture.

10. The method as claimed in claim 5, wherein the C6 aldehyde, a C6 alcohol or a combination thereof is introduced into the fermentable mixture by the introduction of vine leaves.

11. The method as claimed in claim 10, wherein the vine leaves are at least partially crushed vine leaves.

12. The method as claimed in claim 1, wherein the fermentable mixture is fruit juice, must or wort.

13. The method as claimed in claim 12, wherein the fruit juice is white grape juice or red grape juice.

14. The method as claimed in claim 13, wherein the white grape juice or red grape juice is turbid.

15. The method as claimed in claim 12, wherein the fruit juice is juice from the Vitis vinifera species of grape.

16. The method as claimed in claim 15, wherein the fruit juice is juice from Sauvignon Blanc grapes.

17. The method as claimed in claim 1, further including the additional step of agitating the fermentable mixture prior to subjecting the fermentable mixture to fermentation.

18. The method as claimed in claim 1, further including the additional step of introducing a rehydrated yeast mixture into the fermentable mixture before subjecting the fermentable mixture to fermentation.

19. The method as claimed in claim 18, wherein the rehydrated yeast mixture includes active dry wine yeast and a yeast rehydration nutrient.

20. A fermented beverage produced by the method of claim 1.

* * * * *